United States Patent [19]

Winter et al.

[11] 4,382,943
[45] May 10, 1983

[54] ANTI-ALLERGIC ARYL ETHER DERIVATIVES

[75] Inventors: Werner Winter, Heppenheim; Walter-Gunar Friebe, Darmstadt; Androniki Roesch, Mannheim; Otto-Henning Wilhelms, Weinheim-Rittenweier, all of Fed. Rep. of Germany

[73] Assignee: Boehringer Mannheim GmbH, Mannheim, Fed. Rep. of Germany

[21] Appl. No.: 280,434

[22] Filed: Jul. 6, 1981

[30] Foreign Application Priority Data

Jul. 4, 1980 [DE] Fed. Rep. of Germany ....... 3025385

[51] Int. Cl.³ .................. A61K 31/445; C07D 405/06
[52] U.S. Cl. .................... 424/267; 424/258; 546/79; 546/93; 546/108; 546/196
[58] Field of Search .................. 546/108, 93, 79, 196; 424/258, 267

[56] References Cited

U.S. PATENT DOCUMENTS 4,330,549 5/1982 Friebe et al. ................ 424/267

FOREIGN PATENT DOCUMENTS 1404003 8/1975 United Kingdom ............ 546/199

OTHER PUBLICATIONS

*Chemical Abstracts*, 75: 20107s, (1971), [Chatterjee, D., et al., *Indian J. Appl. Chem.*, 1969, 32(1), 65-68].

*Chemical Abstracts*, 51: 10730b, (1957), [Glaz, E., et al., *Arch. Intern. Pharmacodynamie*, 108, 420-30, (1956)].
Bacharach, A., et al., *Biochem. J.*, 36, 407, (1942).

Primary Examiner—Richard A. Schwartz
Attorney, Agent, or Firm—Sprung, Horn, Kramer & Woods

[57] ABSTRACT

An aryl ether derivative of the formula

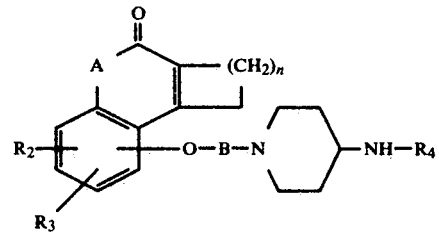

in which
A is an oxygen atom or an $>N-R_1$ grouping,
$R_1$ is a hydrogen atom or a lower alkyl radical,
B is an alkylene radical containing 2 to 4 carbon atoms,
$R_2$ and $R_3$ each independently is a hydrogen or halogen atom, hydroxyl group or lower alkyl, lower alkoxy or lower alkanoyl radical,
$R_4$ is a hydrogen atom or an acyl radical, and
n is an integer from 1 to 5,
or a pharmacologically acceptable salt thereof, which possesses anti-allergic activity.

10 Claims, No Drawings

ANTI-ALLERGIC ARYL ETHER DERIVATIVES

The present invention is concerned with new aryl ether derivatives and with a process for the preparation thereof, as well as with pharmaceutical compositions containing them and with the use thereof for combating allergic diseases.

The aryl ether derivatives according to the present invention are compounds of the general formula:

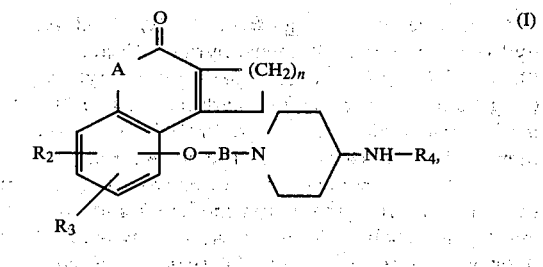

in which
A is an oxygen atom or an $>N-R_1$ grouping,
$R_1$ being a hydrogen atom or a lower alkyl radical,
B is an alkylene radical containing 2 to 4 carbon atoms,
$R_2$ and $R_3$, which can be the same or different, are hydrogen or halogen atoms, hydroxyl groups or lower alkyl, lower alkoxy or lower alkanoyl radicals,
$R_4$ is a hydrogen atom or an acyl radical and n is a whole number from 1 to 5; and the pharmacologically acceptable salts thereof.

Compounds of similar constitution are disclosed in Application Ser. No. 104,205, filed Dec. 17, 1979, now U.S. Pat. No. 4,330,549. In further development of the invention of this previous German Patent Specification, we have now found that the new aryl ether derivatives of general formula (I), which have a tricyclic ring system instead of a bicyclic ring system, also display an outstanding anti-allergic action, which can be demonstrated in the pharmacological test of passive cutaneous anaphylaxis (PCA test) in vivo in rats. Furthermore, they display a strong antihistamine effect, as well as an anti-oedematous and antiphlogistic effectiveness. Therefore, the compounds of general formula (I) according to the present invention can be used especially advantageously for combating allergic diseases, for example asthma, hay fever and urticaria.

The lower alkyl radicals of the substituents $R_1$, $R_2$ and $R_3$ can be straight-chained or branched and contain up to 6 and preferably up to 4 carbon atoms.

The alkylene radical B can be straight-chained or branched, the trimethylene radical being preferred.

The lower alkoxy radicals and lower alkanoyl radicals of the substituents $R_2$ and $R_3$ preferably contain up to 4 carbon atoms.

The halogen atoms $R_2$ and $R_3$ are to be understood to be fluorine, chlorine or bromine atoms.

The preferred value for n is 2, 3 or 4.

The acyl radicals of the substituent $R_4$ can be lower alkanoyl radicals, which are optionally substituted by halogen atoms or aryl radicals, or lower alkenoyl radicals, which are substituted by aryl radicals optionally having one or more substituents, or carbocyclic or heterocyclic aroyl radicals, which are optionally substituted one or more times by halogen, hydroxyl, lower alkyl, lower alkoxy, lower alkoxycarbonyl, lower alkanoyloxy, carboxyl, nitro, amino, lower alkanoylamino, nitrile, trifluoromethyl, carbamoyl, lower alkylthio, lower alkylsulphinyl, lower alkylsulphonyl, lower alkanoyl, aroyl, hydroxy lower alkyl or lower alkoxy lower alkyl. The lower alkyl moieties in the mentioned radicals contain up to 6 and preferably up to 4 carbon atoms, the radicals being straight-chained or branched. The heterocyclic aroyl radical may be, for example, a furancarbonyl, thiophenecarbonyl or pyridinecarbonyl radical and the aroyl radical may be, for example, a benzoyl radical.

Furthermore, the substituent $R_4$ may be the acid residue of a cycloalkylcarboxylic acid, cycloalkyl thereby preferably being understood to be a cyclopropyl, cyclobutyl, cyclopentyl, cyclohexyl or cycloheptyl radical, as well as a carbamoyl radical optionally substituted by lower alkyl or aryl. Furthermore, $R_4$ can also stand for the acid residue of a sulphonic acid, for example of a $C_{1-4}$-alkanesulphonic acid such as methanesulphonic acid or of benzenesulphonic acid.

The term "aryl" in the definition of the substituent $R_4$ preferably means a phenyl or naphthyl radical. Substituents which may optionally be present in the aryl radicals include hydroxyl, halogen, lower alkyl and lower alkoxy, the latter containing up to 6 carbon atoms.

Apart from the compounds mentioned in the examples, the present invention also includes all compounds which display every possible combination of the substituents mentioned in the examples.

According to the process of the present invention for preparing compounds of general formula (I), a compound of the general formula:

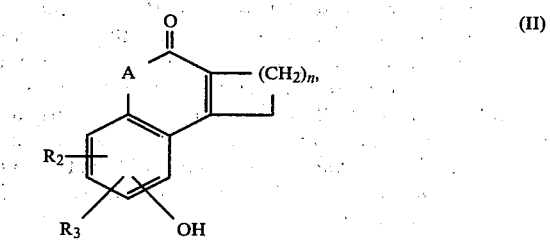

in which A, $R_2$, $R_3$ and n have the same meanings as above, is reacted in per se known manner with a compound of the general formula:

in which X and Y are reactive residues and B has the same meaning as above, and with a compound of the general formula:

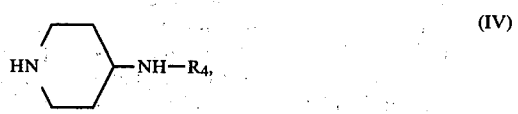

in which $R_4$ has the same meaning as above, whereafter, if desired, the $R_4$ substituent is converted into a different substituent $R_4$ having the above-given meaning, when $R_1$ is a hydrogen atom the product obtained is, if desired, subsequently N-alkylated and the product obtained is, if desired, converted into a pharmacologically acceptable salt.

The reactive residues in the compounds of general formula (III) are preferably chlorine or bromine atoms or mesyloxy or tosyloxy radicals.

The process according to the present invention can be carried out, for example, by first condensing a compound of general formula (III) with a compound of general formula (IV) and the reaction product obtained is isolated. This intermediate is then reacted with a compound of general formula (II). The reaction is preferably carried out in an alkaline medium, for example in a lower alkanol, such as isopropanol, in the presence of sodium isopropanolate, or in dimethylformamide in the presence of potassium carbonate.

According to another variant of the process, a compound of general formula (II) is first reacted with a compound of general formula (III), the reaction mixture obtained being subsequently reacted with a compound of general formula (IV) to give the desired end product of general formula (I).

A subsequent conversion of the substituent $R_4$ in a compound of general formula (I) into a different substituent $R_4$ can take place, for example, by acylating a compound of general formula (I), in which $R_4$ is a hydrogen atom, with a compound of the general formula $R_4$-Z, in which Z is a reactive residue and $R_4$ is an acyl radical. Thus, compounds of general formula (I), in which $R_4$ is a hydrogen atom, are valuable intermediates for the preparation of other compounds of general formula (I), in which $R_4$ is an acyl radical.

The reactive residues Z can be any residues which are used in peptide chemistry for activating carboxylic acids, for example halogen atoms, azide groups and alkoxy, aryloxy and acyloxy radicals.

Starting materials of general formulae (II), (III) and (IV) are known from the literature and can be prepared analogously to processes known from the literature.

The pharmacologically acceptable salts of compounds of general formula (I) can be obtained in the usual way, for example by neutralizing compounds of general formula (I) with non-toxic inorganic or organic acids, such as hydrochloric acid, sulphuric acid, phosphoric acid, hydrobromic acid, acetic acid, lactic acid, citric acid, malic acid, salicyclic acid, malonic acid, maleic acid or succinic acid.

For the preparation of pharmaceutical compositions, the compounds of general formula (I) can be mixed in the usual manner with appropriate pharmaceutical carrier substances, aroma, flavoring and coloring materials and formed, for example into tablets or dragees or, with the addition of appropriate adjuvants, suspended or dissolved in water or in an oil, for example olive oil.

The compounds of general formula (I) can be administered orally or parenterally in liquid or solid form. As injection medium, it is preferable to use water which contains the stabilizing agents, solubilizing agents and/or buffers conventional in the case of injection solutions. Additives of this kind include, for example, tartrate and borate buffers, ethanol, dimethyl sulphoxide, complex formers (such as ethylene-diamine-tetraacetic acid), high molecular weight polymers (such as liquid polyethylene oxide) for viscosity regulation and polyethylene derivatives of sorbitan anhydrides.

Solid carrier materials include, for example, starch, lactose, mannitol, methyl cellulose, talc, highly dispersed silicic acid and high molecular weight polymers (such as polyethylene glycols). Compositions suitable for oral administration can, if desired, contain flavoring and/or sweetening agents.

For external use, the compounds according to the present invention can also be employed in the form of powders or salves. For this purpose, they are mixed, for example, with powdered, physiologically acceptable diluents or with conventional salve bases.

The following examples are given for the purpose of illustrating the present invention:

EXAMPLE 1

7-[3-(4-Benzamidopiperidino)-propoxy]-2,3-dihydrocyclopenta[c][1]benzopyran-4(1H)one hydrochloride A mixture of 10.1 g. (0.05 mole) 2,3-dihydro-7-hydroxycyclopenta[c][1]benzopyran-4(1H)one, 14.0 g. (0.05 mole) 3-(4-benzamidopiperidine)-propyl chloride, 6.9 g. (0.05 mole) potassium carbonate and 100 ml. dimethylformamide is heated to 100° C. for 6 hours and then cooled and filtered. The precipitate obtained (m.p. 218°–220° C.) is washed with water, dissolved in a mixture of dichloromethane and methanol and converted into the hydrochloride by adding an excess of ethereal hydrogen chloride solution. There are obtained 14.8 g. (61% of theory) of the desired hydrochloride; m.p. 274°–275° C.

EXAMPLES 2 TO 34

The following compounds are prepared in a manner analogous to that described in Example 1:

| No. | product and starting materials | Yield % | m.p. °C. |
|---|---|---|---|
| 2 | 2,3-dihydro-7-{3-[4-(4-fluorobenzamido)-piperidino]-propoxy}-cyclopenta[c][1]benzopyran-4(1H)-one hydrochloride from 2,3-dihydro-7-hydroxycyclopenta[c][1]benzopyran-4(1H)-one and 3-[4-(4-fluorobenzamido)-piperidino]-propyl chloride | 49 | 280–281 |
| 3 | 2,3-dihydro-7-{3-[4-(4-methoxybenzamido)-piperidino]-propoxy}-cyclopenta[c][1]benzopyran-4(1H)-one from 2,3-dihydro-7-hydroxycyclopenta[c][1]benzopyran-4(1H)-one and 3-[4-(4-methoxybenzamido)-piperidino]-propyl chloride | 80 | 214–215 |
| 4 | 2,3-dihydro-7-{3-[4-(2-methylbenzamido)-piperidino]-propoxy}-cyclopenta[c][1]benzopyran-4(1H)-one from 2,3-dihydro-7-hydroxycyclopenta[c][1]benzopyran-4(1H)-one and 3-[4-(2-methylbenzamido)-piperidino]-propyl chloride | 46 | 187–188 |
| 5 | 2,3-dihydro-7-{3-[4-(4-methylbenzamido)-piperidino]-propoxy}-cyclopenta[c][1]benzopyran-4(1H)-one hydrogen carbonate from 2,3-dihydro-7-hydroxycyclopenta[c][1]benzopyran-4(1H)-one and 3-[4-(4-methylbenzamido)-piperidino]-propyl chloride | 77 | over 280° C. |
| 6 | 7-{3-[4-(4-t-butylbenzamido)-piperidino]-propoxy}-2,3-dihydrocyclopenta[c][1]benzopyran-4(1H)-one from 2,3-dihydro-7-hydroxycyclopenta[c][1]benzopyran-4(1H)-one and 3-[4-(4-t-butylbenzamido)-piperidino]-propyl chloride | 56 | 223–224 |
| 7 | 7-{3-[4-(4-n-butoxybenzamido)-piperidino]-propoxy}-2,3-dihydrocyclopenta[c][1]benzopyran-4(1H)-one from 2,3-dihydro-7-hydroxycyclopenta[c][1]benzopyran-4(1H)-one and 3-[4-(4-n-butoxybenzamido)- | 62 | 192–193 |

-continued

| No. | product and starting materials | Yield % | m.p. °C. |
|---|---|---|---|
| 8 | 2,3-dihydro-7-[3-(4-phenylacetamido-piperidino)-propoxy]-cyclopenta-[c][1]benzopyran-4(1H)-one from 2,3-dihydro-7-hydroxycyclo-penta[c][1]benzopyran-4(1H)-one and 3-(4-phenylacetamidopiperidino)-propyl chloride | 63 | 173–174 |
| 9 | 7-[3-(4-cyclohexanecarboxamido-piperidino)-propoxy]-2,3-dihydro-cyclopenta[c][1]benzopyran-4(1H)-one from 2,3-dihydro-7-hydroxycyclo-penta[c][1]benzopyran-4(1H)-one and 3-(4-cyclohexanecarboxamido-piperidino)-propyl chloride | 81 | 206–207 |
| 10 | 7-[3-(4-acetamidopiperidino)-propoxy]-2,3-dihydrocyclopenta-[c][1]benzopyran-4(1H)-one from 2,3-dihydro-7-hydroxycyclo-penta[c][1]benzopyran-4(1H)-one and 3-(4-acetamidopiperidino)-propyl chloride | 79 | 182–183 |
| 11 | 7-{3-[4-(4-acetamidobenzamido)-piperidino]-propoxy}-2,3-dihydro-cyclopenta[c][1]benzopyran-4(1H)-one from 2,3-dihydro-7-hydroxycyclo-penta[c][1]benzopyran-4(1H)-one and 3-[4-(4-acetamidobenzamido)-piperidino]-propyl chloride | 70 | 284–285 |
| 12 | 7-[3-(4-benzamidopiperidino)-propoxy]-2,3-dihydro-6-n-propyl-cyclopenta[c][1]benzopyran-4(1H)-one from 2,3-dihydro-7-hydroxy-6-n-propylcyclopenta[c][1]benzopyran-4(1H)-one and 3-(4-benzamido-piperidino)-propyl chloride | 61 | 200–201 |
| 13 | 2,3-dihydro-7-{3-[4-(4-fluorobenz-amido)-piperidino]-propoxy}-6-n-propylcyclopenta[c][1]benzopyran-4(1H)-one from 2,3-dihydro-7-hydroxy-6-n-propylcyclopenta[c][1]benzopyran-4(1H)-one and 3-[4-(4-fluorobenz-amido)-piperidino]-propyl chloride | 82 | 210–211 |
| 14 | 6-acetyl-7-[3-(4-benzamido-piperidino)-propoxy]-2,3-dihydro-cyclopenta[c][1]benzopyran-4(1H)-one from 6-acetyl-2,3-dihydro-7-hydroxycyclopenta[c][1]benzopyran-4(1H)-one and 3-(4-benzamido-piperidino)-propyl chloride | 63 | 218–219 |
| 15 | 7-[3-(4-benzamidopiperidino)-propoxy]-2,3-dihydro-9-hydroxycyclopenta[c][1]-benzopyran-4(1H)-one from 2,3-dihydro-7,9-dihydroxycyclo-penta[c][1]benzopyran-4(1H)-one and 3-(4-benzamidopiperidino)-propyl chloride | 26 | 235–236 |
| 16 | 3-[3-(4-benzamidopiperidino)-propoxy]-7,8,9,10-tetrahydro-6H—dibenzo[b,d]-pyran-6-one hydrochloride from 7,8,9,10-tetrahydro-3-hydroxy-6H—dibenzo[b,d]pyran-6-one and 3-(4-benzamidopiperidino)-propyl chloride | 42 | 258–259 |
| 17 | 3-{3-[4-(4-fluorobenzamido)-piperidino]-propoxy}-7,8,9,10-tetrahydro-6H—dibenzo[b,d]pyran-6-one hydrochloride from 7,8,9,10-tetrahydro-3-hydroxy-6H—dibenzo[b,d]pyran-6-one and 3-[4-(4-fluorobenzamido)-piperidino]-propyl chloride | 47 | 262–263 |
| 18 | 3-{3-[4-(4-methoxybenzamido)-piperidino]-propoxy}-7,8,9,10-tetrahydro-6H—dibenzo[b,d]-pyran-6-one from 7,8,9,10-tetrahydro-3-hydroxy-6H—dibenzo[b,d]pyran-6-one and 3-[4-(4-methoxybenzamido)-piperidino]-propyl chloride | 75 | 215–216 |
| 19 | 3-{3-[4-(4-methylbenzamido)-piperidino]-propoxy}-7,8,9,10-tetrahydro-6H—dibenzo[b,d]pyran-6-one from 7,8,9,10-tetrahydro-3-hydroxy-6H—dibenzo[b,d]pyran-6-one and 3-[4-(4-methylbenzamido)-piperidino]-propyl chloride | 74 | 195–196 |
| 20 | 3-{3-[4-(4-t-butylbenzamido)-piperidino]-propoxy}-7,8,9,10-tetrahydro-6H—dibenzo[b,d]pyran-6-one from 7,8,9,10-tetrahydro-3-hydroxy-6H—dibenzo[b,d]pyran-6-one and 3-[4-(4-t-butylbenzamido)-piperidino]-propyl chloride | 60 | 217–218 |
| 21 | 3-{3-[4-(2-methyl-benzamido)-piperidino]-propoxy}-7,8,9,10-tetrahydro-6H—dibenzo[b,d]pyran-6-one from 7,8,9,10-tetrahydro-3-hydroxy-6H—dibenzo[b,d]pyran-6-one and 3-[4-(2-methylbenzamido)-piperidino]-propyl chloride | 67 | 168–169 |
| 22 | 3-[3-(4-cyclohexanecarboxamido-piperidino)-propoxy]-7,8,9,10-tetrahydro-6H—dibenzo[b,d]pyran-6-one from 7,8,9,10-tetrahydro-3-hydroxy-6H—dibenzo[b,d]pyran-6-one and 3-(4-cyclohexanecarboxamidopiperidino)-propyl chloride | 78 | 207–208 |
| 23 | 3-[3-(4-acetamidopiperidino)-propoxy]-7,8,9,10-tetrahydro-6H—dibenzo[b,d]pyran-6-one from 7,8,9,10-tetrahydro-3-hydroxy-6H—dibenzo[b,d]pyran-6-one and 3-(4-acetamidopiperidino)-propyl chloride | 57 | 167–168 |
| 24 | 3-[3-(4-benzamidopiperidino)-propoxy]-4-n-propyl-7,8,9,10-tetrahydro-6H—dibenzo[b,d]pyran-6-one from 7,8,9,10-tetrahydro-3-hydroxy-4-n-propyl-6H—dibenzo[b,d]pyran-6-one and 3-(4-benzamidopiperidino)-propyl chloride | 47 | 191–192 |
| 25 | 3-{3-[4-(4-fluorobenzamido)-piperidino]-propoxy}-4-n-propyl-7,8,9,10-tetrahydro-6H—dibenzo[b,d]pyran-6-one from 7,8,9,10-tetrahydro-3-hydroxy-4-n-propyl-6H—dibenzo[b,d]pyran-6-one and 3-[4-(4-fluorobenzamido)-piperidino]-propyl chloride | 89 | 207–208 |
| 26 | 3-[3-(4-benzamidopiperidino)-propoxy]-4-methyl-7,8,9,10-tetrahydro-6H—dibenzo[b,d]pyran-6-one from 7,8,9,10-tetrahydro-3-hydroxy-4-methyl-6H—dibenzo[b,d]pyran-6-one and 3-(4-benzamidopiperidino)-propyl chloride | 77 | 224–226 |
| 27 | 4-acetyl-3-[3-(4-benzamido-piperidino)-propoxy]-7,8,9,10-tetrahydro-6H—dibenzo[b,d]pyran-6-one from 4-acetyl-7,8,9,10-tetrahydro-3-hydroxy-6H—dibenzo[b,d]pyran-6-one and 3-(4-benzamidopiperidino)-propyl chloride | 32 | 197–198 |
| 28 | 3-{3-[4-(3-ethylureido)-piperidino]-propoxy}-7,8,9,10-tetrahydro-6H—dibenzo[b,d]pyran-6-one from 7,8,9,10-tetrahydro-3-hydroxy- | 72 | 201–202 |

-continued

| No. | product and starting materials | Yield % | m.p. °C. |
|---|---|---|---|
|  | 6H—dibenzo[b,d]pyran-6-one and 3-[4-(3-ethylureido)-piperidino]-propyl chloride |  |  |
| 29 | 3-[3-(4-benzamidopiperidino)-propoxy]-2-chloro-7,8,9,10-tetrahydro-6H—dibenzo[b,d]pyran-6-one from 2-chloro-7,8,9,10-tetrahydro-3-hydroxy-6H—dibenzo[b,d]pyran-6-one and 3-(4-benzamidopiperidino)-propyl chloride | 83 | 215–216 |
| 30 | 2-[3-(4-benzamidopiperidino)-propoxy]-7,8,9,10-tetrahydro-6H—dibenzo[b,d]pyran-6-one from 7,8,9,10-tetrahydro-2-hydroxy-6H—dibenzo[b,d]pyran-6-one and 3-(4-benzamidopiperidino)-propyl chloride | 69 | 194–195 |
| 31 | 6-[3-(4-benzamidopiperidino)-propoxy]-2,3-dihydro-7-methoxy-cyclopenta[c][1]benzopyran-4(1H)-one from 2,3-dihydro-6-hydroxy-7-methoxycyclopenta[c][1]benzopyran-4(1H)-one and 3-(4-benzamidopiperidino)-propyl chloride | 62 | 156–157 |
| 32 | 3-[3-(4-benzamidopiperidino)-propoxy]-6,7,8,9,10,11-hexahydrobenzo[b]cyclohepta[d]pyran-6-one from 6,7,8,9,10,11-hexahydro-3-hydroxybenzo[b]cyclohepta[d]pyran-6-one and 3-(4-benzamidopiperidino)-propyl chloride | 64 | 185–186 |
| 33 | 7-[3-(4-benzamidopiperidino)-propoxy]-2,3,4,5-tetrahydro-1H—cyclopenta[c]quinolin-4-one from 2,3,4,5-tetrahydro-7-hydroxy-1H—cyclopenta[c]quinolin-4-one and 3-(4-benzamidopiperidino)-propyl chloride | 78 | 273–275 |
| 34 | 3-[3-(4-phenylacetamidopiperidino)-propoxy]-7,8,9,10-tetrahydro-6H—dibenzo[b,d]pyran-6-one from 7,8,9,10-tetrahydro-3-hydroxy-6H—dibenzo[b,d]pyran-6-one and 3-(4-phenylacetamidopiperidino)-propyl chloride | 48 | 172–173 |

EXAMPLE 35

3-[3-(4-Acetamidopiperidino)-propoxy]-7,8,9,10tetrahydro-6H-dibenzo[b,d]pyran-6-one A mixture of 17.3 g. (0.051 mole) 3-(3-bromopropoxy)-7,8,9,10-tetrahydro-6H-dibenzo[b,d]pyran-6-one, 7.3 g. (0.051 mole) 4-acetamidopiperidine, 5.2 g. triethylamine and 100 ml. tetrahydrofuran is heated under reflux for 14 hours and then cooled and filtered. The precipitate obtained is washed with tetrahydrofuran and water and dried in a vacuum. There are obtained 11.3 g. (55% of theory) of the desired compound (m.p. 167°–168° C.) which is identical to the compound of Example 23.

The 3-(3-bromopropoxy)-7,8,9,10-tetrahydro-6Hdibenzo[b,d]pyran-6-one used as starting material can be obtained as follows:

15.2 g. (0.11 mole) Potassium carbonate are added at 75° C. and within the course of 3 hours to a mixture of 21.6 g. (0.1 mole) 7,8,9,10-tetrahydro-3-hydroxy-6H-dibenzo[b,d]pyran-6-one, 60.6 g. 1,3-dibromopropane and 150 ml. butane, whereafter the reaction mixture is heated under reflux for 18 hours, filtered and the filtrate evaporated. The residue is taken up in diethyl ether and washed with a dilute aqueous solution of sodium hydroxide, whereafter the organic phase is evaporated and the residue is triturated with ligroin. There are obtained 20.5 g. (61% of theory) of the desired compound; m.p. 90°–92° C.

EXAMPLE 36

2,3-Dihydro-7-{3-[4-(4-nitrobenzamido)-piperidino]-propoxy}-cyclopenta[c][1]benzopyran-4(1H)-one A mixture of 4.15 g. (0.01 mole) 7-[3-(4-aminopiperidino)-propoxy]-2,3-dihydrocyclopenta[c][1]benzopyran-4(1H)-one dihydrochloride, 2.5 g. sodium bicarbonate and 60 ml. dichloromethane is mixed, while cooling with ice, with a solution of 1.86 g. (0.01 mole) 4-nitrobenzoyl chloride in 20 ml. dichloromethane. The reaction mixture is stirred for 14 hours at ambient temperature, filtered and the precipitate washed with water and dichloromethane and purified by chromatography on silica gel (elution agent dichloromethane:methanol, 9:1 v/v). There are obtained 2.5 g. (51% of theory) of the desired compound; m.p. 212°–213° C.

The 7-[3-(4-aminopiperidino)-propoxy]-2,3-dihydrocyclopenta[c][1]benzopyran-4(1H)-one dihydrochloride used as starting material can be obtained as follows:

A mixture of 76.8 g. (0.2 mole) 7-[3-(4-acetamidopiperidino)-propoxy]-2,3-dihydrocyclopenta[c][1]benzopyran-4(1H)-one (compound of Example 10), 400 ml. dioxane, 200 ml. concentrated hydrochloric acid and 200 ml. water is heated under reflux for 8 hours, cooled and filtered. There are obtained 49.7 g. (60% of theory) of the desired compound; m.p. 225° C.

EXAMPLES 37 TO 44

The following compounds are prepared in a manner analogous to that described in Example 36:

| No. | product and starting materials | Yield % | m.p. °C. |
|---|---|---|---|
| 37 | 7-{3-[4-(4-chlorobenzamido)-piperidino]-propoxy}-2,3-dihydro-cyclopenta[c][1]benzopyran-4(1H)-one from 7-[3-(4-aminopiperidino)-propoxy]-2,3-dihydrocyclopenta-[c][1]benzopyran-4(1H)-one dihydrochloride and 4-chlorobenzoyl chloride | 79 | 213–214 |
| 38 | 2,3-dihydro-7-{3-[4-(thiophene-2-carboxamido)-piperidino]-propoxy}-cyclopenta[c][1]benzopyran-4(1H)-one hydrochloride from 7-[3-(4-aminopiperidino)-propoxy]-2,3-dihydrocyclopenta-[c][1]benzopyran-4(1H)-one dihydrochloride and thiophene-2-carbonyl chloride | 64 | 273–274 |
| 39 | 2,3-dihydro-7-{3-[4-(2-methyl-propionamido)-piperidino]-propoxy}-cyclopenta[c][1]benzopyran-4(1H)-one from 7-[3-(4-aminopiperidino)-propoxy]-2,3-dihydrocyclopenta-[c][1]benzopyran-4(1H)-one dihydrochloride and 2-methylpropionyl chloride | 43 | 186–187 |
| 40 | 3-{3-[4-(4-chlorobenzamido)-piperidino]-propoxy}-7,8,9,10-tetrahydro-6H-dibenzo[b,d]pyran-6-one hydrochloride from 3-[3-(4-aminopiperidino)-propoxy]-7,8,9,10-tetrahydro-6H-dibenzo[b,d]pyran-6-one dihydrochloride and 4 chlorobenzoyl | 73 | 268–269 |

-continued

| No. | product and starting materials | Yield % | m.p. °C |
|---|---|---|---|
| | chloride | | |
| 41 | 3-{3-[4-(5-chloro-2-methoxybenz- amido)-piperidino]-propoxy}- 7,8,9,10-tetrahydro-6H-dibenzo- [b,d]pyran-6-one from 3-[3-(4-aminopiperidino)- propoxy]-7,8,9,10-tetrahydro-6H- dibenzo[b,d]pyran-6-one dihydro- chloride and 5-chloro-2-methoxy- benzoyl chloride | 52 | 170–171 |
| 42 | 3-{3-[4-(furan-2-carboxamido)- piperidino]-propoxy}-7,8,9,10- tetrahydro-6H-dibenzo[b,d]pyran-6- one from 3-[3-(4-aminopiperidino)- propoxy]-7,8,9,10-tetrahydro-6H- dibenzo[b,d]pyran-6-one dihydro- chloride and furan-2-carbonyl chloride | 44 | 183–184 |
| 43 | 3-[3-(4-cyclopropanecarboxamido- piperidino)-propoxy]-7,8,9,10- tetrahydro-6H-dibenzo[b,d]pyran-6- one from 3-[3-(4-aminopiperidino)- propoxy]-7,8,9,10-tetrahydro-6H- dibenzo[b,d]pyran-6-one dihydro- chloride and cyclopropanecarbonyl chloride | 57 | 215–216 |
| 44 | 3-{3-[4-(2-methylpropionamido)- piperidino]-propoxy}-7,8,9,10- tetrahydro-6H-dibenzo[b,d]pyran-6- one from 3-[3-(4-aminopiperidino)- propoxy]-7,8,9,10-tetrahydro-6H- dibenzo[b,d]pyran-6-one dihydro- chloride and 2-methylpropionyl chloride | 78 | 181–182 |

EXAMPLE 45

2,3-Dihydro-7-{3-[4-(pyridine-3-carboxamido)- piperidino]propoxy}-cyclopenta[c][1]benzopyran- 4(1H)-one 1.3 ml. (0.01 mole) Isobutyl chloroformate, dissolved in 10 ml. dichloromethane, is added dropwise at −5° C. to −10° C. to a mixture of 1.23 g. (0.01 mole) nicotinic acid, 40 ml. dichloromethane and 1.4 ml. triethylamine. After stirring the reaction mixture for 15 minutes at −10° C., a slurry of 4.15 g. (0.01 mole) 7-[3-(4-aminopiperidino)-propoxy]-2,3-dihydrocyclopenta[c][1]benzopyran-4(1H)-one dihydrochloride in 30 ml. dichloromethane and 2.8 g. triethylamine is added thereto and the reaction mixture is further stirred for 30 minutes at −10° C., washed with water, mixed with an excess of ethereal hydrogen chloride solution, filtered and the precipitate obtained taken up in water and rendered alkaline with an aqueous solution of sodium hydroxide. There are thus obtained 2.8 g. (62% of theory) of the desired compound; m.p. 199°–200° C.

EXAMPLES 46 TO 48

The following compounds are prepared in a manner analogous to that described in Example 45:

| No. | product and starting materials | Yield % | m.p. °C |
|---|---|---|---|
| 46 | 2,3-dihydro-7-{3-[4-(3,4-dimethoxy- cinnamoylamido)-piperidino]- propoxy}-cyclopenta[c][1]benzopyran- 4(1H)-one from 7-[3-(4-aminopiperidino)- propoxy]-2,3-dihydrocyclopenta- [c][1]benzopyran-4(1H)-one dihydro- chloride and 3,4-dimethoxycinnamic acid | 34 | 210–211 |
| 47 | 3-{3[4-(2-acetoxybenzamido)- piperidino]-propoxy}-7,8,9,10- tetrahydro-6H-dibenzo[b,d]pyran-6- one from 3-[3-(4-aminopiperidino)- propoxy]-7,8,9,10-tetrahydro-6H- dibenzo[b,d]pyran-6-one dihydro- chloride and acetylsalicylic acid | 58 | 176–179 |
| 48 | 2,3-dihydro-7-{3-[4-(2-nitrobenz- amido)-piperidino]-propoxy}-cyclo- penta[c][1]benzopyran-4(1H)-one from 7-[3-(4-aminopiperidino)- propoxy]-2,3-dihydrocyclopenta- [c][1]benzopyran-4(1H)-one dihydro- chloride and 2-nitrobenzoic acid | 45 | 197–198 |

EXAMPLE 49

2,3-Dihydro-7-{3-[4-(N-phenylureido)-piperidino]- propoxy}-cyclopenta[c][1]benzopyran-4(1H)-one A solution of 1.2 g. (0.01 mole) N-phenyl isocyanate in 10 ml. dichloromethane is added dropwise at 5° C. to a mixture of 4.15 g. (0.01 mole) 7-[3-(4-aminopiperidino)propoxy]-2,3-dihydrocyclopenta[c][1]benzopyran-4(1H)-one, 2.52 g. sodium bicarbonate and 60 ml. dichloromethane. The reaction mixture is stirred for 16 hours at ambient temperature, filtered and the precipitate is washed with water and dichloromethane and then purified by chromatography on silica gel (elution agent: dichloromethane:methanol; 9:1 v/v). There are obtained 3.1 g. (67% of theory) of the desired compound; m.p. 207°–208° C.

EXAMPLE 50

2,3-Dihydro-7-[3-(4-ureidopiperidino)-propoxy]- cyclopenta[c][1]benzopyran-4(1H)-one hydrochloride A mixture of 4.15 g. (0.01 mole) 7-[3-(4-aminopiperidino)-propoxy]-2,3-dihydrocyclopenta[c][1]benzopyran-4(1H)-one dihydrochloride, 4.0 g. potassium cyanate, 50 ml. water and 30 ml. 2 N hydrochloric acid is stirred for 3 days at ambient temperature, filtered and the precipitate extracted with hot ethanol. There are thus obtained 2.4 g. (57% of theory) of the desired compound; m.p. 244°–245° C.

EXAMPLE 51

3-{3-[4-(2-Hydroxybenzamido)-piperidino]-propoxy}- 7,8,9,10-tetrahydro-6H-dibenzo[b,d]pyran-6-one A mixture of 5.18 g. (0.01 mole) 3-{3-[4-(2-acetoxybenzamido)-piperidino]-propoxy}-7,8,9,10-tetrahydro-6H-dibenzo[b,d]pyran-6-one (compound of Example 47), 20 ml. dioxane and 20 ml. 6 N hydrochloric acid is heated under reflux for 10 hours, cooled and filtered. There are obtained 3.0 g. (63% of theory) of the desired compound in the form of its hydrochloride; m.p. 232°–234° C. The corresponding free base melts at 209°–211° C.

EXAMPLE 52

7-{3-[4-(4-Aminobenzamido)-piperidino]-propoxy}-2,3-dihydrocyclopenta[c][1]benzopyran-4(1H)-one dihydrochloride In a manner analogous to that described in Example 51, by saponification of 7-{3-[4-(4-acetamidobenzamido)-piperidino]-propoxy}-2,3-dihydrocyclopenta[c][1]benzopyran-4-(1H)-one (compound of Example 11), the desired compound is obtained in a yield of 48% of theory, after chromatography on silica gel; m.p. 267°–269° C.

EXAMPLE 53

7-{3-[4-(2-Aminobenzamido)-piperidino]-propoxy}-2,3dihydrocyclopenta[c][1]benzopyran-4(1H)-one A solution of 1.47 g. (3 mMol) 2,3-dihydro-7-{3-[4-(2-nitrobenzamido)-piperidino]-propoxy}-cyclopenta[c][1]benzopyran-4(1H)-one (compound of Example 48) in 100 ml. ethanol is hydrogenated over 1 g. Raney nickel at ambient temperature and 1 bar hydrogen pressure. After filtration, the filtrate is evaporated and the residue is recrystallized from ethanol. There is obtained 0.85 g. (62% of theory) of the desired compound; m.p. 269°–270° C.

EXAMPLE 54

Tablets are prepared, each of which contains 10 mg. 3-{3-[4-(4-fluorobenzamido)-piperidino]-propoxy}-7,8,9,10-tetrahydro-6H-dibenzo[b,d]pyran-6-one hydrochloride. The tablets are prepared according to the following formulation:

| | |
|---|---|
| 3-{3-[4-(4-fluorobenzamido)-piperidino]-propoxy}-7,8,9,10-tetrahydro-6H-dibenzo-[b,d]pyran-6-one hydrochloride | 10 g. |
| lactose | 80 g. |
| starch | 29 g. |
| magnesium stearate | 1 g. |

The active compound is finely powdered and mixed with the lactose and starch. The mixture is then granulated in conventional manner. The magnesium stearate is added to the granulate and the mixture pressed to give 1000 tablets, each of which has an individual weight of 0.12 g.

The foregoing compounds can be used as such or they can be converted to salts with pharmacologically acceptable acids. They can be administered to patients orally, as pills, tablets, capsules, powders and the like. The preferred form of oral administration is a tablet containing 10 to 300 mg of active compound, which nearly complies with the typical daily dosage. A preferred dosage is 30 to 100 mg.

The compounds can also be administered parenterally. Injection solutions containing 0.05 to 50 mg/ml of injection solution are administered.

The superior activity of the novel compounds is shown by comparing the inhibition of antigen induced bronchospasms in passively sensitized guinea pigs. Specifically, tests were run as follows:

Preparation of Antiserum

The antigen is twice recrystallized egg albumin. Equal volumes of saline solution of antigen (5 mg/ml) and Freund's complete adjuvant were emulsified and 0.15 ml injected into each hind foot of adult male guinea pigs (Davies and Johnson: Int. Arch. Allergy 41,648–654 (1971)).

The animals were bled and the pooled serum stored at −20° C.

Passive Sensitization

Injections of 0.5 ml antiserum of 1:50 dilution were given i.v. 24–48 h before challenge.

Guinea pigs were anaesthetized with phenobarbital sodium (40 mg/kg i.p.). Cannulae were tied into the trachea and the jugular vein and the lung inflated with a pump at a rate of 72 strokes/min and a constant stroke volume of 6–8 ml.

Bronchospasm, provoked by injecting ovalbumin i.v. was measured as described by Konzett, H. and R. Rössler, "Versuchsanordnung su Untersuchungen an der Bronchialmuskulatur" Naunyn-Schmiedebergs, Arch. exp. Path. Pharmak. 195, 71–74 (1940) and modified by Collier, H. O. J., J. A. Holgate and M. Schachter: "The Bronchoconstrictor Action of Bradykinin in the Guinea-Pig" Brit. J. Pharmacol. 15, 290 (1960).

The drugs were applied per os 60 minutes before the antigen.

For calculation the following formula was used:

% Bronchospasm $(b-a)/(m-a) \times 100$ b = Bronchospasm after antigen injection, measured in mm from tracing m = maximum height of tracing in mm with arm of the tracheacannula clamped a = pre injection height of the tracing in mm % inhibition of bronchospasm was calculated by comparing control groups with drug pretreated groups 3 minutes after antigen application.

The results obtained, statistically confirmed using the t-test, are set forth in the following table:

TABLE

| Inhibition of antigen induced bronchospasm (Br Sp) in passively sensitized guinea pigs | | |
|---|---|---|
| Example | % inhibition Br Sp dose mg/kg p.o. | % |
| 1 | 0.38 | 47 |
| 2 | 0.38 | 67 |
| 17 | 0.38 | 58 |
| 14 | 0.38 | 79 |
| 4 | 0.75 | 76 |
| 8 | 0.75 | 70 |
| 18 | 0.75 | 87 |
| | 0.38 | 35 |
| 21 | 0.75 | 78 |
| | 0.38 | 51 |
| Terbutalin | 0.1 | 12 |
| | 1.0 | 52 |

Terbutalin = 5-{2-[(1,1-Dimethylethyl)-amino]-1-hydroxyethyl}-1,3-benzenediol

It will be understood that the specification and examples are illustrative but not limitative of the present invention and that other embodiments within the spirit and scope of the invention will suggest themselves to those skilled in the art.

We claim:

1. An aryl ether derivative of the formula

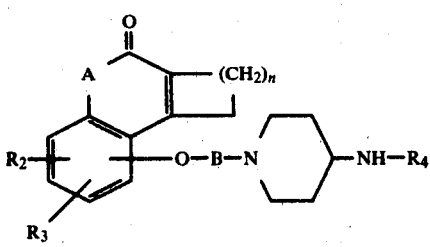

in which

A is an oxygen atom or an >N—R₁ grouping,

R₁ is a hydrogen atom or a lower alkyl radical,

B is an alkylene radical containing 2 to 4 carbon atoms,

R₂ and R₃ each independently is a hydrogen or halogen atom, hydroxyl group or lower alkyl, lower alkoxy or lower alkanoyl radical, R₄ is a hydrogen atom; a C₁₋₄-alkanoyl radical optionally substituted by halogen, phenyl or naphthyl; a C₁₋₄-alkenoyl radical optionally substituted by phenyl or naphthyl; a benzoyl, furancarbonyl, thiophen carbonyl or pyridinecarbonyl radical optionally substituted by halogen, hydroxyl, lower alkyl, lower alkoxy, lower alkoxycarbonyl, lower alkanoyloxy, carboxyl, nitro, amino, lower alkanoylamino, nitrile, trifluoromethyl, carbamoyl, lower alkylthio, lower alkylsulphinyl, lower alkylsulphonyl, lower alkanoyl, benzoyl, hydroxy lower alkyl or lower alkoxy lower alkyl; a C₃-C₇-cycloalkylcarbonyl or carbamoyl radical optionally substituted by lower alkyl, phenyl or naphthyl; a C₁₋₄-alkanesulphonic acid radical; or a phenyl- or naphthyl-sulphonic acid radical, and n is an integer from 1 to 5, or a pharmacologically acceptable salt thereof.

2. An aryl ether derivative or salt thereof according to claim 1, in which

A is an oxygen atom, >N—H or >N—C₁₋₄-alkyl,

B is —CH₂—CH₂—CH₂—,

R₂ and R₃ each independently is hydrogen, fluorine, chlorine, bromine, OH or C₁₋₄-alkyl, alkoxy or alkanoyl, n is 2, 3 or 4.

3. A compound according to claim 1, wherein such compound is 7-[3-(4-benzamidopiperidino)-propoxy]-2,3-dihydrocyclopenta[c][1]benzopyran-4(1H)one, or a pharmacologically acceptable salt thereof.

4. A compound according to claim 1, wherein such compound is 2,3-dihydro-7-{3-[4-(4-fluorobenzamido)-piperidino]-propoxy}-cyclopenta[c][1]benzopyran-4(1H)-one, or a pharmacologically acceptable salt thereof.

5. A compound according to claim 1, wherein such compound is 6-acetyl-7-[3-(4-benzamidopiperidino)-propoxy]-2,3-dihydrocyclopenta[c][1]benzopyran-4(1H)-one, or a pharmacologically acceptable salt thereof.

6. A compound according to claim 1, wherein such compound is 3-{3-[4-(4-fluorobenzamido)-piperidino]-propoxy}-7,8,9,10-tetrahydro-6H-dibenzo[b,d]pyran-6-one, or a pharmacologically acceptable salt thereof.

7. A compound according to claim 1, wherein such compound is 3-{3-[4-(2-methyl-benzamido)-piperidino]-propoxy}-7,8,9,10-tetrahydro-6H-dibenzo[b,d]-pyran-6-one, or a pharmacologically acceptable salt thereof.

8. An anti-allergic composition of matter comprising an anti-allergically effective amount of a compound or salt according to claim 1 and a pharmacologically acceptable diluent.

9. A method of combating an allergic response in a patient which comprises administering to such patient an anti-allergically effective amount of a compound or salt according to claim 1.

10. The method according to claim 9, wherein such compound is

7-[3-(4-benzamidopiperidino)-propoxy]-2,3-dihydrocyclopenta[c][1]benzopyran-4(1H)one, 2,3-dihydro-7-{3-[4-(4-fluorobenzamido)-piperidino]-propoxy}-cyclopenta[c][1]benzopyran-4(1H)-one, 6-acetyl-7-[3-(4-benzamidopiperidino)-propoxy]-2,3-dihydrocyclopenta[c][1]benzopyran-4(1H)-one, 3-{3-[4-(4-fluorobenzamido)-piperidino]-propoxy}-7,8,9,10-tetrahydro-6H-dibenzo[b,d]pyran-6-one, or 3-{3-[4-(2-methyl-benzamido)-piperidino]-propoxy}-7,8,9,10-tetrahydro-6H-dibenzo[b,d]-pyran-6-one, or a pharmacologically acceptable salt thereof.

* * * * *